United States Patent [19]

Layman

[11] Patent Number: 4,460,355
[45] Date of Patent: Jul. 17, 1984

[54] FLUID PRESSURE MONITORING SYSTEM

[75] Inventor: Douglas C. Layman, San Diego, Calif.

[73] Assignee: IVAC Corporation, San Diego, Calif.

[21] Appl. No.: 387,672

[22] Filed: Jun. 11, 1982

[51] Int. Cl.³ .............................................. A61M 1/03
[52] U.S. Cl. .................................... 604/118; 604/121; 222/40
[58] Field of Search ......... 128/673, 674, 675, DIG. 3, 128/DIG. 12, DIG. 13; 417/38, 63; 604/65, 66, 67, 118, 121, 50, 151, 153, 245; 222/40

[56] References Cited

U.S. PATENT DOCUMENTS 3,799,702 3/1974 Weishaar ................................ 417/38
4,098,274 7/1978 Ebling et al. ................. 128/DIG. 3
4,277,227 7/1981 Jenkins ................................... 417/63

Primary Examiner—Edward M. Coven
Attorney, Agent, or Firm—Fulwider, Patton, Rieber, Lee & Utecht

[57] ABSTRACT

Method and apparatus for detecting occlusions in a parenteral administration system of a type having a peristaltic pump for pumping a fluid through a feeding tube to a patient. A pressure transducer measures the cyclicly varying pressure of the fluid in the feeding tube and produces a corresponding pressure signal, and a comparator compares the pressure signal to a selected one of several thresholds, depending on the current stage of the pumping cycle. An occlusion alarm is actuated whenever the selected threshold is exceeded.

21 Claims, 2 Drawing Figures

FLUID PRESSURE MONITORING SYSTEM

BACKGROUND OF THE INVENTION

This invention relates generally to systems for monitoring fluid pressure, and, more particularly, to parenteral administration systems that monitor the pressure of the fluid being administered and actuate an alarm if a prescribed threshold is exceeded.

In recent years, parenteral administration systems having positive pressure intravenous (IV) infusion pumps have come into increasing usage, primarily because the flow rates of the fluid these systems administer can be controlled with great accuracy and precision. The infusion pumps are typically of the peristaltic type, having a plurality of cam follower fingers that massage an IV tube progressively along its axis, to drive a fluid through the tube under positive pressure. Exemplary peristaltic pumps are disclosed in U.S. Pat. No. 3,736,930, issued to Heinz W. Georgi and entitled +Parenteral Administration Fluid Flow Control System" and in a copending and commonly-assigned application for U.S. patent, Ser. No. 281,848, filed July 9, 1981, in the names of Stephen H. O'Leary et al and entitled "Method and Apparatus for Fluid Flow Control."

The parenteral administration systems described above frequently include pressure monitoring devices for use in detecting high fluid pressures, which ordinarily indicate the occurrence of an occlusion somewhere in the system. Typically, a pressure transducer monitors the pressure of the fluid being administered, producing a corresponding pressure signal, and a comparator compares the pressure signal to a prescribed threshold, actuating an aural and visual alarm if the threshold is exceeded.

Such pressure monitoring devices have not proven entirely effective in parenteral administration systems of the type having peristaltic-type infusion pumps, primarily because the cyclic nature of the pumping action causes pressure spikes that sometimes can be improperly detected as occlusions. It should therefore be appreciated that there still is a need for an effective pressure monitoring system that can detect occlusions in a parenteral administration system of the type that pumps a fluid in a cyclic fashion. The present invention fulfills this need.

SUMMARY OF THE INVENTION

The present invention is embodied in a pressure detection apparatus for use in a parenteral administration system of a type that cyclicly pumps a fluid through a feeding tube to a patient, each pumping cycle having a period of reduced fluid flow. The apparatus includes pressure transducer means for measuring the pressure of the fluid being pumped through the tube and for producing a corresponding pressure signal. In accordance with the invention, the apparatus further includes comparator means for comparing the pressure signal to a prescribed threshold only during the periods of reduced fluid flow in the successive pumping cycles, along with alarm means for producing an alarm whenever the comparator means determines that the pressure signal exceeds the threshold. In this way, the undesired effects of the pressure spikes caused by the cyclic pumping action are eliminated.

More particularly, the pressure detection apparatus of the invention is of particular use in a system that includes an infusion pump such as a peristaltic-type pump, in which the fluid flow rate is reduced substantially to zero for a prescribed time period during each pumping cycle. The comparator means compares the pressure signal to the threshold only after the pressure transients caused by the cyclic pumping are substantially reduced in magnitude. Conveniently, this comparison can occur at a prescribed time during each period of reduced flow.

The pressure transducer means preferably monitors the feeding tube and produces the pressure signal continuously during each pumping cycle. At times other than the prescribed time of each period of reduced flow, the comparator means compares the pressure signal to a second prescribed threshold, which is greater than the first threshold. The second threshold is selected to be sufficiently high that pressure spikes are not detected as occlusions. The first threshold is preferably selectively variable, and the second threshold is preferably a multiple of the first threshold.

Other aspects and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
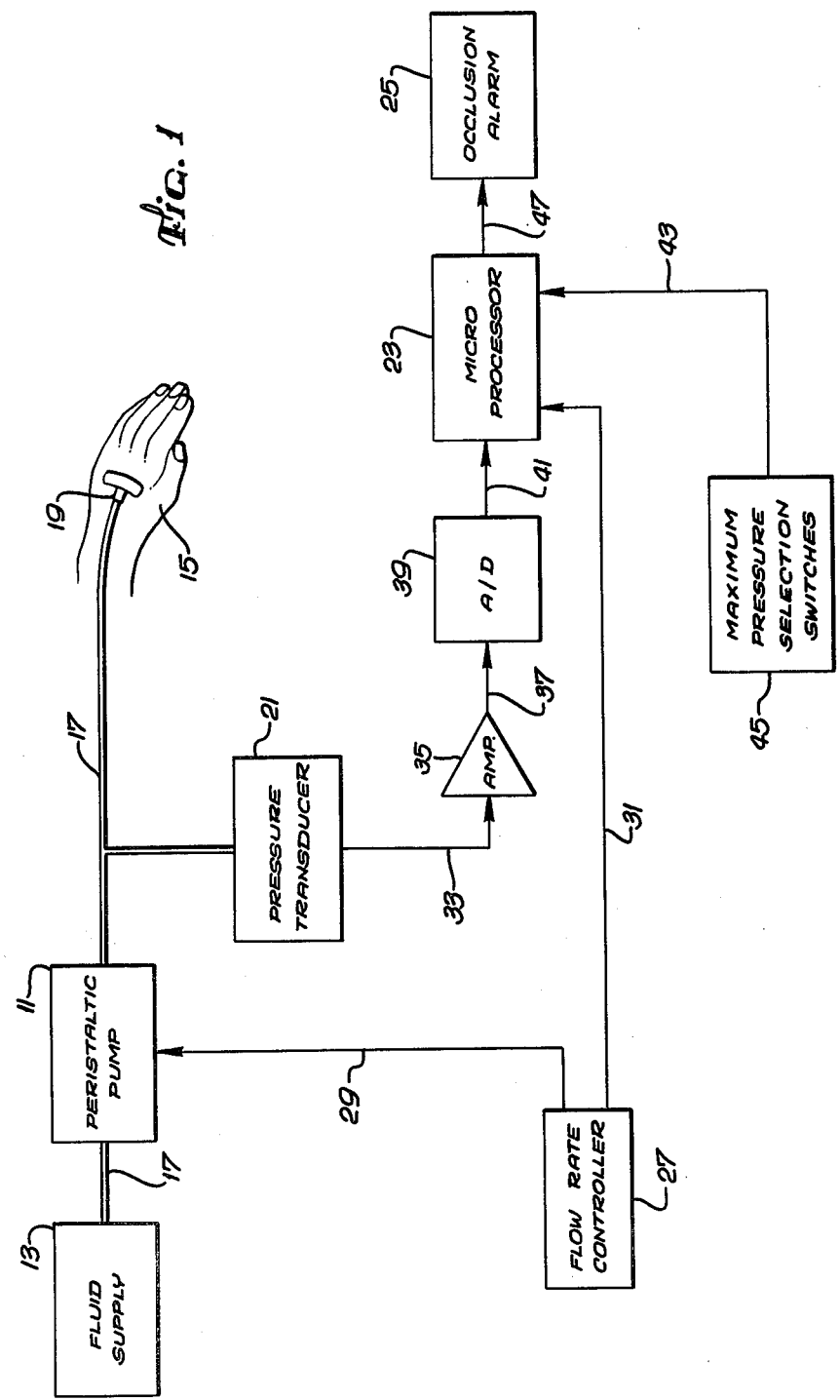
FIG. 1 is a simplified block diagram of a parenteral administration system having a pressure detection apparatus embodying the present invention.

Referring now to the drawings, and particularly to FIG. 1, there is shown a parenteral administration system having a peristaltic pump 11 for pumping a fluid from a fluid supply 13 to a patient 15 via a feeding tube 17 and needle 19. A pressure transducer 21 monitors the pressure of the fluid in the feeding tube and produces a corresponding pressure signal. A microprocessor 23 compares the pressure signal to one of several thresholds in a prescribed fashion, to detect occlusions in the system, actuating an occlusion alarm 25 whenever the selected threshold is exceeded.

The cyclic nature of the pumping action of the peristaltic pump 11 produces a flow rate and fluid pressure that are correspondingly cyclic. Also, during each pumping cycle, there is a relatively short period of prescribed duration in which fluid flow through the pump is reduced substantially to zero.

In accordance with the invention, the microprocessor 23 compares the pressure signal to a first prescribed pressure threshold only at a prescribed time in each pumping cycle of the peristaltic pump 11. In particular, this comparison is made only during the period of substantially reduced flow in each pumping cycle, whereby the undesired effects of pressure spikes are substantially eliminated.

More particularly, the peristaltic pump 11 is preferably of a type that includes a plurality of cam follower fingers that massage the feeding tube 17 progressively along its axis, to drive fluid through the tube under positive pressure. A flow rate controller 27 couples a drive signal over line 29 to the pump, to drive the fingers at a prescribed, selectable rate. The controller can advantageously correspond to that described in detail in a copending and commonly-assigned application for U.S. patent, Ser. No. 281,848, filed on July 9, 1981, in the names of Stephen H. O'Leary et al and entitled "Method and Apparatus for Fluid Flow Control." This copending application is incorporated by reference.

The flow rate controller 27 preferably includes a stepper motor for driving the peristaltic pump 11 through its successive pumping cycles. Each cycle corresponds to a prescribed number of steps, and a counter in the controller indicates the current stage of the pumping cycle. The period of reduced fluid flow occurs in each pumping cycle when the last cam follower finger is pinching off the feeding tube 17. When the count in the controller's counter reaches a point indicating that about 60 percent of the period of reduced flow has elapsed, it is determined that the pressure in the feeding tube has reached a stable level, unaffected by pressure transients of the cyclic pumping action. The controller then outputs a signal for coupling on line 31 to the microprocessor 23, indicating that it should compare the pressure signal to the first prescribed pressure threshold at that time.

The pressure transducer 21 continuously monitors the pressure in the feeding tube 17, whereby the resultant pressure signal varies cyclicly with the cyclic pumping action. The pressure signal is coupled over line 33 from the transducer to an amplifier 35 for amplification, and in turn over line 37 to an analog-to-digital converter 39 for conversion to a digital format. The digitized pressure signal is coupled over lines 41 to the microprocessor 23. A signal representing the pressure threshold to which the digitized pressure signal is compared in the microprocessor is supplied to the microprocessor on line 43 from a set of maximum pressure selection switches 45. These switches permit the operator to select the specific pressure threshold at which the occlusion alarm 25 is actuated.

At the prescribed time in the period of reduced flow of each pumping cycle, the microprocessor 23 compares the digitized pressure signal input to it on lines 41 to the threshold indicated by the maximum pressure selection switches 45. If the threshold is exceeded, the microprocessor outputs an alarm signal on line 47 for coupling to the occlusion alarm 25, to provide both an aural and visual alarm. As previously mentioned the particular time in each pumping cycle at which this comparison is made preferably occurs when about sixty percent of the period of reduced flow has elapsed. At that time, the fluid pressure in the feeding tube should have achieved a stable level.

At all other times during the pumping cycle, the microprocessor 23 compares the digitized pressure signal to prescribed upper and lower pressure thresholds of about 740 and 100 centimeters of water, respectively. The upper threshold represents a pressure level above which the pressure transducer can be damaged; if it is exceeded, the microprocessor immediately outputs an alarm signal to the occlusion alarm 25.

If the microprocessor 23 determines that the digitized pressure signal is between the prescribed upper and lower pressure thresholds, it makes a further comparison of the pressure signal to a threshold that corresponds to three times the threshold indicated by the maximum pressure selection switches 45. Again, if this threshold is exceeded, the microprocessor couples an alarm signal over line 47 to the occlusion alarm 25.

Prior to comparing the digitized pressure signal to the various thresholds, the microprocessor 23 low-pass filters the signal to reduce the magnitude of transient pressure spikes caused by any movement of the feeding tube 17 or by action of the peristaltic pump 11. This filtering can be conveniently performed by averaging the current pressure reading with the last-computed average, which is preferably weighted about three times more than the current reading. This is accomplished by adding the current reading to three times the last-computed average, and by then dividing the sum by four to produce a new average.

Figure 2:
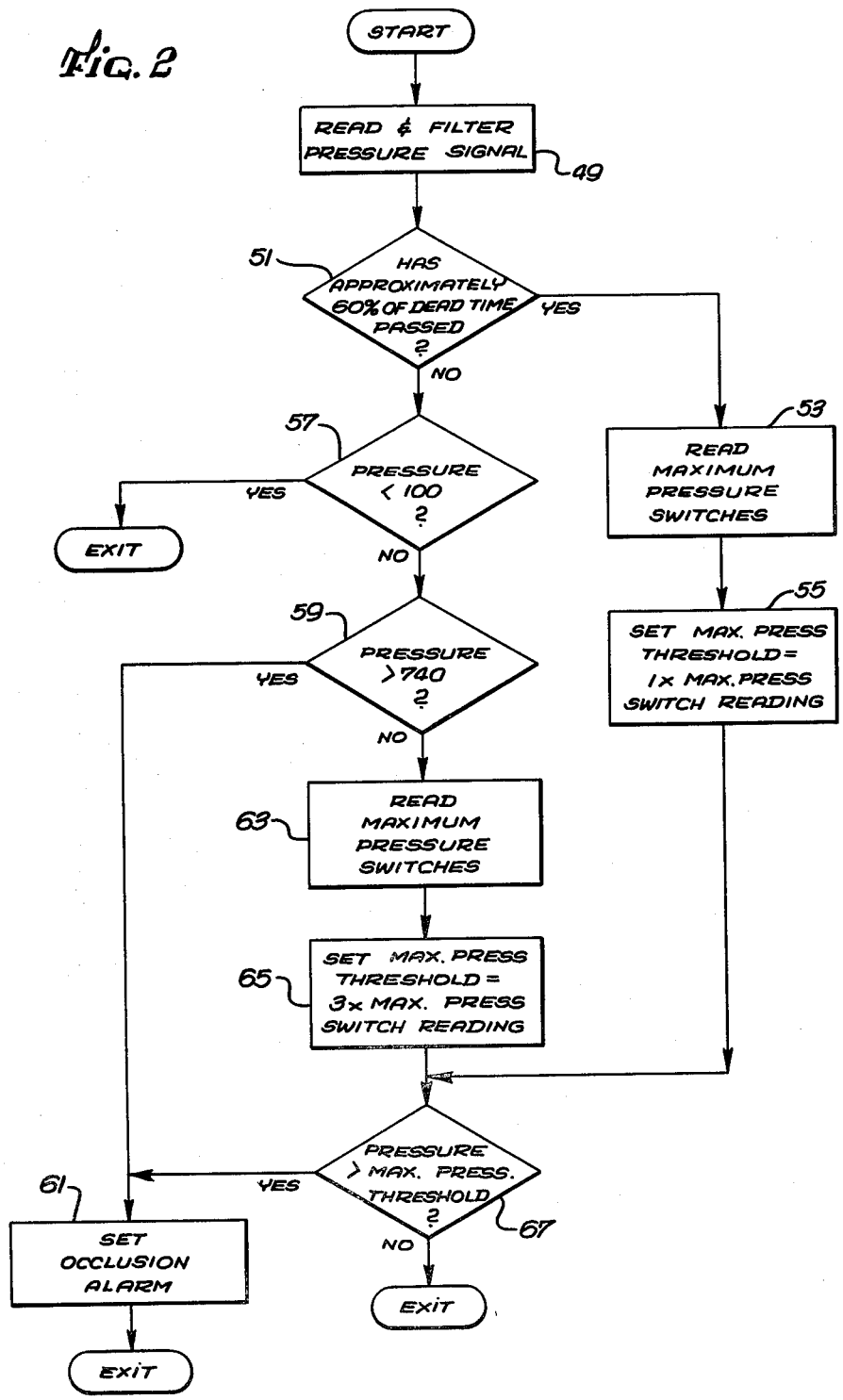
FIG. 2 is a flowchart showing, in simplified form, a pressure detection routine followed by the microprocessor of FIG. 1 in carrying out the invention.

Referring now to FIG. 2, there is shown a simplified flowchart of a pressure detection routine performed by the microprocessor 23 in reading the pressure signal, comparing it to the various pressure thresholds and actuating the occlusion alarm 25. In an initial step 49, the microprocessor reads the digitized pressure signal supplied to it on lines 41 and low-pass filters the signal to remove undesired pressure spikes. At step 51, it is determined whether or not the system's pumping cycle is currently about sixty percent of the way through the period of reduced flow rate. If that point of the pumping cycle has been reached, the maximum pressure switches 45 are read at step 53, and the pressure threshold is set to be equal to one times the pressure indicated by the switches, at step 55.

If it is determined at step 51 that the pumping cycle is at a point other than sixty percent of the way through the period of reduced flow, i.e., either earlier or later in the period of reduced flow or outside the period of reduced flow altogether, it is determined at step 57 whether or not the pressure signal is less than 100 centimeters of water. If it is less than this threshold, the microprocessor immediately exits this pressure detection routine. On the other hand, if the pressure is not determined to be less than 100 centimeters of water, the microprocessor determines, at step 59, whether or not the pressure exceeds 740 centimeters of water. If it does exceed this threshold, the program proceeds immediately to step 61, where the microprocessor outputs an alarm signal for coupling on line 47 to the occlusion alarm 25. On the other hand, if it is determined at step 59 that the pressure does not exceed 740 centimeters of water, the maximum pressure switches 45 are read at step 63, and the pressure threshold is set to be equal to three times the pressure indicated by the switches, at step 65.

Finally, it is determined at step 67 whether or not the current filtered pressure signal exceeds the pressure threshold, which was computed in either of steps 55 or 65. If the threshold is exceeded, it is deduced that an occlusion of some kind exists and an alarm signal is output on line 47 for coupling to the occlusion alarm 25. On the other hand, if it is determined at step 67 that the filtered pressure signal does not exceed the computed threshold, the alarm signal is not produced and the microprocessor 23 exits the pressure detection routine.

Attached as an appendix is a listing of the specific instructions used to carry out the flowchart of FIG. 2 on an 8080-type microprocessor.

It should be appreciated from the foregoing description that the present invention provides an improved method and apparatus for detecting occlusions in a parenteral administration system of the type including a cyclic infusion pump. The apparatus continuously compares a signal representing the fluid pressure to one of several prescribed pressure thresholds, depending on the particular stage of the system's pumping cycle. If the pressure signal ever exceeds the selected threshold, an occlusion alarm is actuated.

Although the present invention has been described in detail with reference to the presently preferred embodiment, it should be understood by those of ordinary skill in the art that various modifications can be made, without departing from the invention. Accordingly, the invention is limited only by the appending claims.

I claim:

1. Pressure detection apparatus for use in a parenteral administration system of a type having a pump that cyclicly pumps a fluid through a feeding tube to a patient, each pumping cycle having a period of reduced fluid flow, and further having means for producing a control signal indicative of the timing of the period of reduced fluid flow in each pumping cycle, the apparatus comprising:
   pressure transducer means for measuring the pressure of the fluid the pump is pumping through the feeding tube to the patient and for producing a corresponding pressure signal;
   comparator means, responsive to the control signal, for comparing the pressure signal to a prescribed threshold only during the periods of reduced fluid flow in the successive pumping cycles of the pump; and
   alarm means for producing an alarm whenever the comparator means determines that the pressure signal exceeds the threshold.

2. Pressure detection apparatus as defined in claim 1, wherein the comparator means compares the pressure signal to the threshold only after pressure transients caused by the cyclic nature of the pumping are substantially reduced in magnitude.

3. Pressure detection apparatus as defined in claim 2, wherein the comparator means compares the pressure signal to the threshold at a prescribed time in the period of reduced fluid flow in each of the successive pumping cycles.

4. Pressure detection apparatus as defined in claim 1, wherein the pressure transducer means produces the pressure signal continuously during each pumping cycle.

5. Pressure detection apparatus as defined in claim 4, wherein the comparator means compares the pressure signal to a second prescribed threshold at times other than the successive periods of reduced fluid flow.

6. Pressure detection apparatus as defined in claim 5, wherein the second threshold is greater than, and a multiple of, the first threshold.

7. Pressure detection apparatus as defined in claim 1, wherein the prescribed threshold used by the comparator means is selectively variable.

8. A parental administration system comprising:
   peristaltic pump means for cyclicly pumping a fluid through a feeding tube to a patient, each pumping cycle having a period of prescribed duration in which fluid flow is substantially reduced;
   means for producing a control signal indicative of the period of reduced fluid flow in each pumping cycle;
   pressure transducer means for measuring the pressure of the fluid being pumped through the feeding tube and for producing a corresponding pressure signal;
   comparator means, responsive to the control signal, for comparing the pressure signal to a prescribed threshold only during the periods of reduced fluid flow of the successive pumping cycles; and
   alarm means for producing an alarm whenever the comparator means determines that the pressure signal exceeds the threshold.

9. A parenteral administration system as defined in claim 8, wherein the comparator means compares the pressure signal to the threshold only at a prescribed time in the period of reduced fluid flow in each of the successive pumping cycles.

10. A parenteral administration system as defined in claim 8, wherein:
    the pressure transducer means produces the pressure signal continuously during each pumping cycle; and
    the comparator compares the pressure signal to a second prescribed threshold at times other than the successive periods of substantially reduced fluid flow.

11. Pressure detection apparatus for use in a parenteral administration system of a type having a pump that pumps a fluid through a feeding tube to a patient at a flow rate that varies in a cyclic fashion, and further having means for producing a control signal indicative of the stage of the variable flow rate in each pumping cycle, the apparatus comprising:
    pressure transducer means for measuring the pressure of the fluid the pump is pumping through the feeding tube to the patient and for producing a corresponding pressure signal;
    comparator means, responsive to the control signal, for comparing the pressure signal to a prescribed threshold that varies in accordance with pumping cycle of the pump; and
    alarm means for producing an alarm whenever the comparator means determines that the pressure signal exceeds the threshold.

12. Pressure detection apparatus as defined in claim 11, wherein:
    each pumping cycle includes a period of substantially reduced fluid flow; and
    the prescribed threshold is a first level at a prescribed time in each period of reduced fluid flow and a second, higher level at all other times.

13. A parenteral administration system comprising:
    peristaltic pump means for cyclicly pumping a fluid through a feeding tube to a patient, each pumping cycle having a period of prescribed duration in which fluid flow is substantially reduced;
    means for producing a control signal indicative of the timing of the period of reduced fluid flow in each pumping cycle of the peristaltic pump means;
    pressure transducer means for continuously measuring the pressure of the fluid being pumped through the feeding tube and for producing a corresponding pressure signal;
    comparator means, responsive to the control signal, for comparing the pressure signal to a first prescribed threshold at a prescribed time in each of the successive periods of reduced fluid flow and for comparing the pressure signal to a second prescribed threshold at other times, the second threshold being higher than the first threshold; and
    alarm means for producing an alarm whenever the comparator means determines that the pressure signal exceeds either of the two thresholds.

14. A method for parenteral administration comprising steps of:
- cyclicly pumping a fluid through a feeding tube to a patient, each pumping cycle having a period of reduced fluid flow;
- producing a control signal indicative of the timing of the period of reduced fluid flow in each pumping cycle;
- measuring the pressure of the fluid being pumped through the feeding tube and producing a corresponding pressure signal;
- comparing the pressure signal to a prescribed threshold only when the control signal indicates a period of reduced fluid flow of the successive pumping cycles is occurring; and
- producing an alarm whenever the step of comparing determines that the pressure signal exceeds the threshold.

15. A method as defined in claim 14, wherein the step of comparing occurs only after transients caused by the cyclic nature of the pumping are substantially reduced in magnitude.

16. A method as defined in claim 15, wherein the step of comparing occurs at a prescribed time in the period of reduced fluid flow in each of the successive pumping cycles.

17. A method as defined in claim 14, wherein the step of measuring occurs continuously during each pumping cycle.

18. A method as defined in claim 17, and further including a step of comparing the pressure signal to a second prescribed threshold at times other than the successive periods of reduced fluid flow.

19. A method as defined in claim 14, and further including a step of selecting the threshold used in the step of comparing.

20. A method for detecting occlusions in a parenteral administration system of a type having a pump that pumps a fluid through a feeding tube to a patient at a flow rate that varies in cyclic fashion and further having means for producing a control signal indicative of the timing of the variable flow rate in each pumping cycle, comprising steps of:
- measuring the pressure of the fluid the pump is pumping through the feeding tube to the patient and producing a corresponding pressure signal;
- comparing the pressure signal to a prescribed threshold that varies in accordance with the control signal; and
- producing an alarm whenever the step of comparing determines that the pressure signal exceeds the threshold.

21. A method as defined in claim 20, wherein:
- each pumping cycle includes a period of substantially reduced fluid flow; and
- the prescribed threshold used in the step of comparing is a first level at a prescribed time in each period of reduced fluid flow and a second, higher level at all other times.

* * * * *